United States Patent [19]

Schoeppl et al.

[11] 4,041,222
[45] Aug. 9, 1977

[54] RUBBER MIXTURES HAVING IMPROVED SURFACE TACK

[75] Inventors: Hubert Schoeppl, Mannheim; Harro Petersen, Frankenthal; Gerhard Paulus, Weinheim; Hubertus Queins, Friedelsheim, all of Germany

[73] Assignee: BASF Aktiengesellschaft, Ludwigshafen (Rhine), Germany

[21] Appl. No.: 622,251

[22] Filed: Oct. 14, 1975

Related U.S. Application Data

[62] Division of Ser. No. 493,779, Aug. 1, 1974, abandoned.

Foreign Application Priority Data

Aug. 13, 1973  Germany ............................ 2340048

[51] Int. Cl.² ................................................ C08K 5/34
[52] U.S. Cl. ........................................ 526/6; 260/30.2; 260/251 R; 260/761
[58] Field of Search ................ 526/6; 260/30.2, 760, 260/761, 791, 726, 739, 251 R

[56] References Cited

U.S. PATENT DOCUMENTS

| 2,871,211 | 1/1959 | Mika | 260/251 R |
| 3,450,703 | 6/1969 | Petersen | 260/251 R |
| 3,891,608 | 6/1975 | Petersen | 526/6 |

FOREIGN PATENT DOCUMENTS 35-2171  3/1960  Japan

*Primary Examiner*—Paul R. Michl
*Attorney, Agent, or Firm*—Keil, Thompson & Shurtleff

[57] ABSTRACT

2-Oxotetrahydropyrimidines of the general formula:

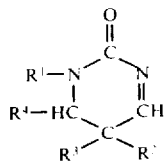

in which $R^1$ to $R^4$ denote hydrogen or alkyl of from 1 to 20 carbon atoms and may be the same or different. The compounds are suitable for use as tackifiers for rubber. They produce excellent and long-lasting surface tack in rubber mixtures.

1 Claim, No Drawings

RUBBER MIXTURES HAVING IMPROVED SURFACE TACK

This is a division, of application Ser. No. 493,779 filed Aug. 1, 1974 now abandoned.

This application discloses and claims subject matter described in German patent application P 23 40 048.8, filed Aug. 8, 1973, which is incorporated herein by reference.

This invention relates to oxotetrahydropyrimidines and to their use as tackifiers for rubber.

Non-vulcanized rubber articles such as panels or strips must show surface tack when being made up into finished articles, since such tackiness is essential for effecting shaping prior to vulcanization. It also ensures that no air is trapped between the individual layers of rubber so that subsequent vulcanization thereof produces good adhesion of said layers. It is also desirable that the rubber should remain tacky during the usual storage periods prior to shaping.

Surface tack is usually improved by adding tackifiers to the rubber mixture. Such substances are rosin, cumarone resin, resins based on hydrocarbons, phenol/formaldehyde resins and polyadducts of phenols and acetylene. However, the surface tack achieved therewith is unsatisfactory in many cases and, above all, it declines very rapidly over a storage period of several days.

We have now found that 2-oxotetrahydropyrimidines produce an excellent and long-lasting surface tack in rubber mixtures. These compounds have the general formula:

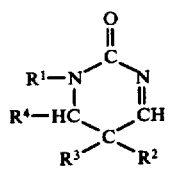

in which the radicals $R^1$ to $R^4$ each denotes hydrogen or alkyl of from 1 to 20 and preferably of from 1 to 8 and more preferably of from 1 to 3 carbon atoms and may be the same or different.

These oxotetrahydropyrimidines may be prepared by eliminating water of alcohols $R^5OH$ from 2-oxo-4-hydroxy-(alkoxy)hexahydropyrimidines of the general formula II below at elevated temperatures, preferably temperatures above 100°:

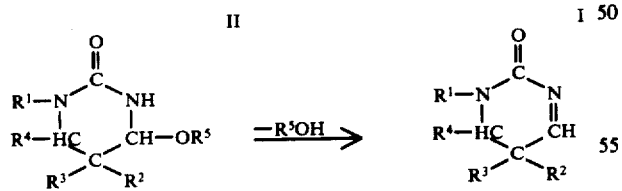

The elimination of water or alcohol $R^5OH$ from the compounds of formula II is accelerated both by acids and by bases or water-extracting means.

The manufacture of compounds of the general formula II is described for example in German Pat. Nos. 1,230,805 and 1,231,247.

Suitable rubbers are all conventional natural and synthetic rubbers such as homopolymers of butadiene or isoprene or their copolymers with styrene or acrylonitrile, butyl rubber, ethylene/propylene rubbers and polyacrylate rubbers. The oxotetrahydropyrimidines should be present in the rubber mixture in amounts of from 1 to 20 and preferably from 2 to 10 parts for every 100 parts of rubber. The mixtures may also contain conventional additives for rubber, e.g. fillers such as carbon black, silicic acid or talcum; softeners such as naphthene oils or paraffins; and flameproofing and odor-improving agents. Incorporation is carried out on conventional rubber-processing machines such as kneaders or rollers at temperatures above about 120° C.

In the following Examples the parts are by weight.

EXAMPLE 1

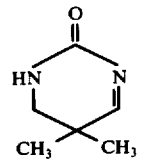

500 parts of 2-oxo-4-methoxy-5,5-dimethylhexahydropyrimidine are heated at from 170° to 190° C in a 1 l. stirred flasked equipped with a metal stirrer and distilling means. At from about 125° to 130° C, the elimination of methanol commences and this is collected in a receiver. The elimination of methanol is complete after heating for from 2 to 2.5 hours at from 70° to 190° C. The liquid residue is cooled and crystallization occurs. There are obtained 368 parts of 2-oxo-5,5-dimethyltetrahydropyrimidine, equivalent to a yield of 92.5% of theory. The melting point of the compound is from 155° to 165° C (with decomposition).

EXAMPLE 2

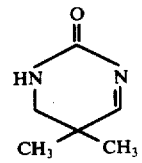

In the manner described in Example 1, 500 parts of 2-oxo-4-hydroxy-5,5-dimethylhexahydropyrimidine are heated for 2 hours at from 180° to 200° C with stirring. The eliminated water is distilled off. There are obtained 360 parts of 2-oxo-5,5-dimethyltetrahydropyrimidine. Yield 82% of theory.

EXAMPLE 3

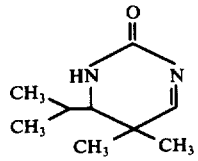

100 parts of 2-oxo-4-methoxy-5,5-dimethyl-6-isopropyl-hexahydropyrimidine are heated in a stirred vessel equipped with a metal stirrer and distilling means for 2 hours at 200°–210° C with stirring, the distillable products being collected in a receiver. The contents of the vessel are cooled to room temperature to cause crystallization. There are obtained 496 parts of 2-oxo-5,5-dimethyl-6-isopropyltetrahydropyrimidine, equivalent to a yield of 55% of theory. The melting point is from 125° to 135° C (with decomposition). The distillate consists of methanol and a further elimination product of the formula $(CH_3)_2CH-CH=N-CH=C(CH_3)_2$.

EXAMPLE 4

5 parts of 2-oxo-5,5-dimethyltetrahydropyrimidine are kneaded into a natural rubber mixture composed of:
100 parts of masticated natural rubber,
50 parts of carbon black and
5 parts of naphthene oil as softener (NAFTOLEN ZD) at 120° C. The surface tack achieved thereby is very much greater than that of the untreated mixture and that of the mixture which has been treated with 5 parts of a commercial tackifier based on a hydrocarbon resin. A measure of the surface tack is given by determining the force required to pull apart two strips of the rubber mixture being tested. The strips are previously pressed together under a specific pressure. To avoid tearing of the mixture during this test, when the surface tack is high, the strips are laminated to a flexible fabric. The adhesion is given in kg and relates to an effective strip width of 6 mm. The measuring range is from 0 to a maximum of 2 kg (Bussemaker, van Beek, Rubber Chemistry and Technology 37 (1964), No. 1 "A new type of tackmeter").

| Results | | | | |
|---|---|---|---|---|
| | | Strip storage time | | |
| Additive | — | 1 day | 2 days | 5 days |
| none | >2 | 0.6 | 0.5 | 0.4 |
| hydrocarbon resin | >2 | 1.2 | 0.8 | 0.5 |
| 2-oxo-5,5-dimethyltetra-hydropyrimidine | >2 | >2 | >2 | >2 |

EXAMPLE 5

3.3 parts of 2-oxo-5,5-dimethyl-6-isopropyltetrahydropyrimidine are added to an oil-extended butadiene/styrene mixture at 120° C.
The composition of the mixture is as follows:
50 parts of butadiene/styrene rubber
50 parts of oil-extended butadiene/styrene rubber
50 parts of carbon black
20 parts of talcum
10 parts of softener.

| Results | | | | |
|---|---|---|---|---|
| | | Strip storage time | | |
| Additive | — | 1 day | 2 days | 5 days |
| none | >2 | 1.2 | 0.5 | 0.4 |
| hydrocarbon resin | >2 | 1.4 | 0.8 | 0.4 |
| 2-oxo-5,5-dimethyl-6-iso-propyltetrahydropyrimidine | >2 | >2.0 | >2.0 | >2.0 |

We claim:
1. Rubber mixtures containing from 1 to 20 parts of a 2-oxotetrahydropyrimidine for every 100 parts of rubber wherein said 2-oxotetrahydropyrimidines having the formula:

$$R^1-N\overset{\overset{O}{\|}}{\underset{R^4-HC}{C}}\overset{N}{\underset{C}{\|}}CH$$
$$R^3 \quad R^2$$

in which the radicals $R^1$ to $R^4$ each denotes hydrogen or alkyl of from 1 to 20 carbon atoms and may be the same or different.

* * * * *